(12) United States Patent
Huang et al.

(10) Patent No.: US 8,715,564 B2
(45) Date of Patent: *May 6, 2014

(54) METHOD OF FABRICATING AN IMPLANTABLE MEDICAL DEVICE WITH BIAXIALLY ORIENTED POLYMERS

(75) Inventors: Bin Huang, Pleasanton, CA (US); Stephen Schaible, Anaheim, CA (US); Richard Kaufman, Los Gatos, CA (US); Jim Kennedy, Murrieta, CA (US); David C. Gale, San Jose, CA (US); Suresh Amin, Temecula, CA (US); John Guardiano, Menifee, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,562

(22) Filed: May 3, 2012

(65) Prior Publication Data

US 2012/0217672 A1    Aug. 30, 2012

Related U.S. Application Data

(62) Division of application No. 12/806,785, filed on Aug. 19, 2010, now Pat. No. 8,192,678, which is a division of application No. 10/899,948, filed on Jul. 26, 2004, now abandoned.

(51) Int. Cl.
*B29C 49/04*    (2006.01)

(52) U.S. Cl.
USPC ............................. 264/540; 264/515; 264/563

(58) Field of Classification Search
None
See application file for complete search history.

(56) References Cited

U.S. PATENT DOCUMENTS

| | | |
|---|---|---|
| 3,636,956 A | 1/1972 | Schneider |
| 4,136,143 A | 1/1979 | Lupke et al. |
| 4,547,416 A | 10/1985 | Reed et al. |
| 4,698,196 A | 10/1987 | Fabian et al. |
| 4,702,884 A | 10/1987 | Goldstein |
| 4,957,687 A | 9/1990 | Akman et al. |
| 4,987,025 A | 1/1991 | Shiraki et al. |
| 5,087,394 A | 2/1992 | Keith |
| 5,108,416 A | 4/1992 | Ryan et al. |
| 5,116,365 A | 5/1992 | Hillstead |
| 5,147,302 A | 9/1992 | Euteneuer et al. |
| 5,500,013 A | 3/1996 | Buscemi et al. |
| 5,628,786 A | 5/1997 | Banas et al. |

(Continued)

FOREIGN PATENT DOCUMENTS

| | | |
|---|---|---|
| EP | 0 583 170 | 2/1994 |
| EP | 1 800 628 | 6/2007 |

(Continued)

OTHER PUBLICATIONS

International Search Report for PCT/US2005/025759 filed Jul. 20, 2005, mailed Dec. 27, 2005, 15 pgs.

(Continued)

*Primary Examiner* — Monica Huson
(74) *Attorney, Agent, or Firm* — Squire Sanders (US) LLP

(57) ABSTRACT

Methods and systems for manufacturing an implantable medical device, such as a stent, from a tube with desirable mechanical properties, such as improved circumferential strength and rigidity, are described herein. Improved circumferential strength and rigidity may be obtained by inducing molecular orientation in materials for use in manufacturing an implantable medical device. Methods of inducing circumferential molecular orientation by inducing circumferential flow in a molten polymer are disclosed.

19 Claims, 5 Drawing Sheets

(56) References Cited

U.S. PATENT DOCUMENTS

| | | |
|---|---|---|
| 5,670,161 A | 9/1997 | Healy et al. |
| 5,725,547 A | 3/1998 | Chuter |
| 5,780,807 A | 7/1998 | Saunders |
| 5,891,386 A | 4/1999 | Deitermann et al. |
| 5,906,759 A | 5/1999 | Richter |
| 5,922,005 A | 7/1999 | Richter et al. |
| 6,360,577 B2 | 3/2002 | Austin |
| 6,500,146 B1 | 12/2002 | Pinchuk et al. |
| 6,572,813 B1 | 6/2003 | Zhang et al. |
| 6,626,939 B1 | 9/2003 | Burnside et al. |
| 6,645,422 B2 | 11/2003 | Jung et al. |
| 7,066,952 B2 | 6/2006 | Igaki |
| 7,070,615 B1 | 7/2006 | Igaki |
| 7,083,639 B2 | 8/2006 | Guinan et al. |
| 7,128,868 B2 | 10/2006 | Eidenschink |
| 7,637,886 B2 | 12/2009 | Herweck et al. |
| 8,192,678 B2 | 6/2012 | Huang et al. |
| 2001/0014821 A1 | 8/2001 | Juman et al. |
| 2002/0077592 A1 | 6/2002 | Barry |
| 2002/0138133 A1 | 9/2002 | Lenz et al. |
| 2002/0151965 A1 | 10/2002 | Roth |
| 2003/0009151 A1 | 1/2003 | Wang |
| 2003/0028241 A1 | 2/2003 | Stinson |
| 2003/0028246 A1 | 2/2003 | Palmaz et al. |
| 2003/0055488 A1 | 3/2003 | Igaki |
| 2003/0083732 A1 | 5/2003 | Stinson |
| 2003/0187158 A1 | 10/2003 | Preuschen et al. |
| 2003/0208254 A1 | 11/2003 | Shortt |
| 2003/0226833 A1 | 12/2003 | Shapovalov et al. |
| 2004/0000361 A1 | 1/2004 | Trozera |
| 2004/0098090 A1 | 5/2004 | Williams et al. |
| 2005/0004663 A1 | 1/2005 | Llanos et al. |
| 2005/0137678 A1 | 6/2005 | Varma |
| 2005/0177130 A1 | 8/2005 | Konstantino et al. |
| 2005/0187615 A1 | 8/2005 | Williams et al. |
| 2005/0196485 A1 | 9/2005 | Cass et al. |
| 2006/0020330 A1 | 1/2006 | Huang et al. |
| 2006/0076708 A1 | 4/2006 | Huang et al. |
| 2006/0211952 A1 | 9/2006 | Kennedy |
| 2006/0224226 A1 | 10/2006 | Huang et al. |
| 2007/0253996 A1 | 11/2007 | Bin et al. |
| 2007/0253999 A1 | 11/2007 | Huang et al. |
| 2007/0282433 A1 | 12/2007 | Limon et al. |
| 2007/0290412 A1 | 12/2007 | Capek et al. |
| 2007/0293938 A1 | 12/2007 | Gale et al. |
| 2008/0001333 A1 | 1/2008 | Kleine et al. |
| 2009/0001633 A1 | 1/2009 | Limon et al. |
| 2009/0005860 A1 | 1/2009 | Gale et al. |
| 2009/0012598 A1 | 1/2009 | Abbate et al. |
| 2009/0146348 A1 | 6/2009 | Huang et al. |

FOREIGN PATENT DOCUMENTS

| | | |
|---|---|---|
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 03/034940 | 5/2003 |
| WO | WO 2004/067262 | 8/2004 |
| WO | WO 2006/014747 | 2/2006 |

OTHER PUBLICATIONS

Answers.com blow molding; retrieved from www.answers.com/blow%20moldinq#Stretch_blow_molding, Jun. 26, 2009, 11 pgs.
www.engineeringtoolbox.com/thermal/conductivity/d_429.html., Jun. 26, 2009, 4 pgs.

METHOD OF FABRICATING AN IMPLANTABLE MEDICAL DEVICE WITH BIAXIALLY ORIENTED POLYMERS

CROSS-REFERENCE TO RELATED APPLICATIONS

This application is a divisional of application Ser. No. 12/806,785, filed Aug. 19, 2010, now U.S. Pat. No. 8,192,678 which is a divisional of application Ser. No. 10/899,948, filed Jul. 26, 2004, now abandoned, each of which is incorporated herein by reference.

BACKGROUND OF THE INVENTION

1. Field of the Invention

This invention relates to methods of fabricating implantable medical devices such as stents.

2. Description of the State of the Art

This invention relates to radially expandable endoprostheses which are adapted to be implanted in a bodily lumen. An "endoprosthesis" corresponds to an artificial implantable medical device that is placed inside the body. A "lumen" refers to a cavity of a tubular organ such as a blood vessel. A stent is an example of these endoprostheses. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

Stents have been made of many materials including metals and polymers. Polymer materials include both nonbioerodable and bioerodable plastic materials. The cylindrical structure of stents is typically composed of a scaffolding that includes a pattern or network of interconnecting structural elements or struts. The scaffolding can be formed from wires, tubes, or planar films of material rolled into a cylindrical shape. In addition, a medicated stent may be fabricated by coating the surface of either a metallic or polymeric scaffolding with a polymeric carrier. The polymeric carrier can include an active agent or drug. Furthermore, the pattern that makes up the stent allows the stent to be radially expandable and longitudinally flexible. Longitudinal flexibility facilitates delivery of the stent and rigidity is needed to hold open a body lumen. The pattern should be designed to maintain the longitudinal flexibility and rigidity required of the stent. A stent should also have adequate strength in the circumferential direction.

A number of techniques have been suggested for the fabrication of stents from tubes and planar films or sheets. One such technique involves laser cutting or etching a pattern onto a material. Laser cutting may be performed on a planar film of a material which is then rolled into a tube. Alternatively, a desired pattern may be etched directly onto a tube. Other techniques involve cutting a desired pattern into a sheet or a tube via chemical etching or electrical discharge machining. Laser cutting of stents has been described in a number of publications including U.S. Pat. No. 5,780,807 to Saunders, U.S. Pat. No. 5,922,005 to Richter and U.S. Pat. No. 5,906,759 to Richter.

A treatment involving a stent involves both delivery and deployment of the stent. "Delivery" refers to introducing and transporting the stent through a bodily lumen to a region requiring treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

It is desirable for a stent to have certain mechanical properties to facilitate delivery and deployment of a stent. For example, longitudinal flexibility is important for successful delivery of the stent. In addition, circumferential strength and rigidity and are vital characteristics in deployment and for holding open a body lumen. As indicated above, the pattern of the stent may be designed to provide longitudinal flexibility and rigidity.

However, the characteristics of the material of which a stent is composed also affects the mechanical properties of the stent. An advantage of stents fabricated from polymers is that they tend to possess greater flexibility than metal stents. Other potential shortcomings of metal stents include adverse reactions from the body, nonbioerodability, and non-optimal drug-delivery. However, a potential shortcoming of polymer stents compared to metal stents, is that polymer stents typically have less circumferential strength and rigidity. Inadequate circumferential strength potentially contributes to relatively high recoil of polymer stents after implantation into vessels. Furthermore, another potential problem with polymer stents is that struts can crack during crimping, especially for brittle polymers. Therefore, methods of manufacturing polymer stents that improve circumferential strength and rigidity are desirable. The embodiments of the present invention address the issue of improving circumferential strength and rigidity in polymer stents.

SUMMARY OF THE INVENTION

Various embodiments of the present invention include a method of manufacturing a stent, comprising: introducing a polymer into a forming apparatus comprising a first annular member disposed within a second annular member, wherein the polymer is conveyed through an annular chamber as an annular film between the annular members; inducing circumferential flow in the annular film; forming a tube from the annular film; and fabricating a scaffold comprising a plurality of interconnecting struts from the tube.

Further embodiments of the present invention include a method of manufacturing a stent, comprising: introducing a polymer into a forming apparatus comprising a first annular member disposed within a second annular member, wherein the polymer is conveyed through an annular chamber as an annular film between the annular members; inducing spiral circumferential molecular orientation in the annular polymer film with a spiral channel on at least a portion of a surface of the first annular member or the second annular member;

forming a tube from the annular film; and fabricating a scaffold comprising a plurality of interconnecting struts from the tube.

BRIEF DESCRIPTION OF THE DRAWINGS

FIGS. 4B-7 depict an axial cross-section of a forming apparatus.

DETAILED DESCRIPTION OF THE INVENTION

Figure 1:
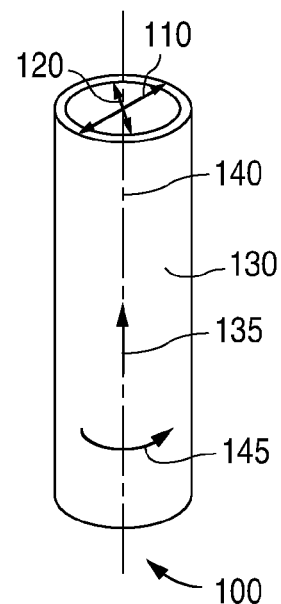
FIG. 1 depicts a tube.

For the purposes of the present invention, the following terms and definitions apply:

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

The term "elastic deformation" refers to deformation of an object in which the applied stress is small enough so that the object retains its original dimensions or essentially its original dimensions once the stress is released.

"Elastic limit" refers to the maximum stress that a material will withstand without permanent deformation.

The term "plastic deformation" refers to permanent deformation that occurs in a material under stress after elastic limits have been exceeded.

"Strength" refers to the maximum stress along an axis in testing which a material will withstand prior to fracture. The ultimate strength is calculated from the maximum load applied during the test divided by the original cross-sectional area.

"Modulus" may be defined as the ratio of the stress or force per unit area applied to a material divided by the amount of strain resulting form the applied force.

"Strain" refers to the amount of elongation or compression that occurs in a material at a given stress or load.

"Elongation" may be defined as the increase in length which occurs when subjected to stress. It is typically expressed as a percentage of the original length.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. A second fluid can act as a non-solvent for the impurity. "Non-solvent" is defined as a substance incapable of dissolving the other substance. The non-solvent should be capable of dissolving only less than 0.1 mg of the polymer in 1 ml of the non-solvent at ambient temperature and ambient pressure, and more narrowly only less than 0.05 mg in 1 ml at ambient temperature and ambient pressure.

Implantable medical device is intended to include self-expandable stents, balloon-expandable stents, stent-grafts, and grafts. The structural pattern of the device can be of virtually any design. The device can also be made partially or completely from a biodegradable, bioabsorbable, or biostable polymer. The polymer may be purified to remove undesirable materials.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and eventual absorption and elimination of the polymer can be caused by, for example, hydrolysis, metabolic processes, bulk or surface erosion, and the like. If the material is used in coating applications, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate an implantable medical device using the methods disclosed herein include poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

It is well known by those skilled in the art of polymer technology that mechanical properties of a polymer may be modified by processes that alter the molecular structure of the polymer. Polymers in the solid state may be completely amorphous, partially crystalline, or almost completely crystalline. Crystalline regions in a polymer are characterized by alignment of polymer chains along the longitudinal or covalent axis of the polymer chains. An oriented crystalline structure tends to have high strength and a high modulus (low elongation with applied stress) along an axis of alignment of polymer chains. A high modulus material tends to have a high degree of rigidity. Therefore, a region of a polymeric material with a high degree of oriented crystalline structure tends to have high strength and rigidity along an axis of polymer chain alignment. Therefore, it may be desirable to incorporate processes that induce molecular orientation of polymer chains along a preferred axis or direction into manufacturing methods of implantable medical devices.

Furthermore, molecular orientation in a polymer may be induced, and hence mechanical properties modified, by applying stress to the polymer. The degree of molecular orientation induced with applied stress may depend upon the temperature of the polymer. For example, below the glass transition temperature, $T_g$, of a polymer, polymer segments may not have sufficient energy to move past one another. In general, molecular orientation may not be induced without sufficient segmental mobility.

The "glass transition temperature," $T_g$, is the temperature at which the amorphous domains of a polymer change from a brittle vitreous state to a solid deformable state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility. Generally, flexible main-chain components lower the $T_g$; bulky side-groups raise the $T_g$; increasing the length of flexible side-groups lowers the $T_g$; and increasing main-chain polarity increases the $T_g$. Additionally, the presence of crosslinking polymeric components can increase the observed $T_g$ for a given polymer.

Above $T_g$, molecular orientation may be readily induced with applied stress since rotation of polymer chains, and hence segmental mobility, is possible. Between $T_g$ and the melting temperature of the polymer, $T_m$, rotational barriers exist, however, the barriers are not great enough to substantially prevent segmental mobility. As the temperature of a polymer is increase above $T_g$, the energy barriers to rotation decrease and segmental mobility of polymer chains tend to increase. As a result, as the temperature increases, molecular orientation is more easily induced with applied stress.

Moreover, application of stress to a polymer between $T_g$ and the melting temperature of the polymer, $T_m$, may induce molecular orientation of the polymer, and hence, modify its mechanical properties. However, rearrangement of polymer chains may take place when a polymer is stressed in an elastic region and in a plastic region of the polymer material. A polymer stressed beyond its elastic limit to a plastic region generally retains its stressed configuration and corresponding induced molecular orientation when stress is removed. The polymer chains may become oriented in the direction of the applied stress which results in an oriented crystalline structure. The stressed polymer material may have a higher tensile strength in the direction of the applied stress.

Furthermore, as indicated above, a plastically deformed material tends to retain its deformed configuration once the deforming stress is removed. Stress applied to the material subsequent to the initial deforming stress tends not to cause further deformation of the material unless the applied stress is greater than the initial stress level that caused the deformation. Therefore, the behavior of a plastically deformed material may be more predictable within a range of stress. The stress range may be less than the initial stress applied that caused the plastic deformation.

Additionally, application of heat with stress may facilitate deformation of a polymer under stress, and hence, modification of the mechanical properties of the polymer. A polymer deformed elastically with stress facilitated with applied heat may retain induced molecular orientation by cooling the polymer before relaxing to an unstrained state.

Furthermore, above $T_m$, a polymer exists as a polymer melt or in a molten state. In a polymer melt, there is a very small barrier to bond rotation, and hence, segmental mobility of polymer chains is very high. As suggested above, the higher the temperature, the greater the segmental mobility, or generally, the more intense the molecular motion. Therefore, applying stress to a polymer melt may also induce molecular orientation. Stress may be applied to a polymer melt in the form of a film as an isotropic stress or pressure which results in expansion of the film, as in a bubble. The expansion may result in circumferential molecular orientation in a direction of induced strain along the surface of the expanded film. Alternatively, a shear stress may be applied which induces flow in the polymer melt. The molecular orientation may tend to be in the direction or along an axis of applied shear stress or flow. However, due to intense molecular motion, the induced molecular orientation is not stable. Once the shear stress is removed or the flow slows or stops, molecular motion may tend to dissipate the molecular orientation. The highest temperature at which molecular orientation is stable is less than or equal to the $T_m$ of the polymer. Therefore, it may be necessary to reduce the temperature of a polymer melt below $T_m$ to inhibit or prevent dissipation of molecular orientation.

Various embodiments of methods for manufacturing an implantable medical device with desirable mechanical properties are described herein. Some embodiments of manufacturing an implantable medical device may include fabricating the implantable medical device from a polymer conduit or tube. The tube may be cylindrical or substantially cylindrical in shape. For example, FIG. 1 depicts a tube 100. Tube 100 is a cylinder with an outside diameter 110 and an inside diameter 120. FIG. 1 also depicts a surface 130 and a cylindrical axis 140 of tube 100. When referred to below, unless otherwise specified, the "diameter" of the tube refers to the outside diameter of tube. In some embodiments, the diameter of the tube prior to fabrication of the implantable medical device may be between about 0.5 mm and about 3.0 mm. In other embodiments, the diameter of the tube prior to fabrication may be between about 1 mm and 2 mm. An example of a tube prior to fabrication may include one with a diameter of 2.13 mm (0.084 in).

Figure 2:
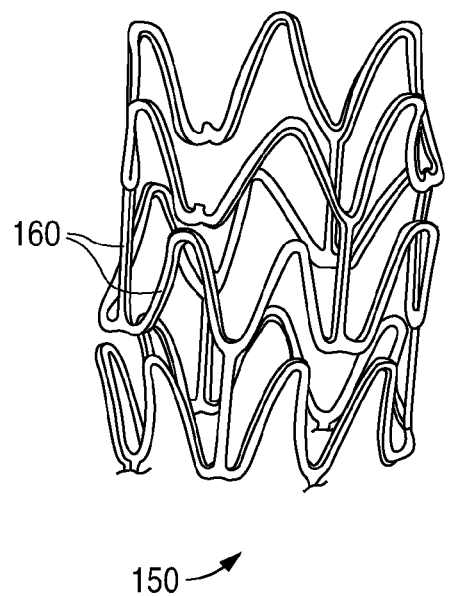
FIG. 2 depicts a three-dimensional rendering of an implantable medical device with a pattern.

An implantable medical device may be fabricated from a polymer tube. Fabrication may include forming a pattern that includes at least one interconnecting element or strut on the tube. In some embodiments, forming a pattern on the tube may include laser cutting a pattern on the tube. Representative examples of lasers that may be used include an excimer, carbon dioxide, and YAG. In other embodiments, chemical etching may be used to form a pattern on the tube. It is desirable to use a laser cutting technique which minimizes a size of a heat affected zone. A heat affected zone refers to a region of a target material affected by the heat of the laser. Heat from the laser may tend to melt at least a portion of polymer in the heat affected zone. The molecular orientation induced by applied stress may then be dissipated in the melted portion. The corresponding favorable change in mechanical properties may also be reduced or substantially eliminated. FIG. 2 depicts a three-dimensional view of an implantable medical device 220 which may be formed from tube 100 in FIG. 1.

FIG. 2 depicts an implantable medical device 150 that includes a pattern of struts 160. The final etched out pattern should not be limited to what has been illustrated as other stent patterns are easily applicable with the method of the invention.

As discussed above, it is desirable for a polymer tube for use in manufacturing an implantable medical device to have adequate strength in the longitudinal direction, as shown by an arrow 135 in FIG. 1. Also, strength circumferential direction, as shown by an arrow 145 in FIG. 1, is also very important. A tube with biaxial molecular orientation, or equivalently, a tube with a desired degree of molecular orientation in both the longitudinal and the circumferential directions may possess the desirable mechanical properties. Implantable medical devices, such as stents, fabricated from tubes with biaxial orientation may possess mechanical properties similar to or better than metal stents with an acceptable wall thickness and strut width. Several embodiments of manufacturing implantable medical devices with biaxial orientation, and hence, with desired mechanical properties are described herein.

Polymer tubes may be formed by means of various types of forming methods, including, but not limited to extrusion or injection molding. Alternatively, a polymer tube may be formed from sheets or films that are rolled and bonded. In extrusion, a polymer melt is conveyed through an extruder which is then formed into a tube. Extrusion tends to impart large forces on the molecules in the longitudinal direction of the tube due to shear forces on the polymer melt. The shear forces arise from forcing the polymer melt through a die and pulling and forming the polymer melt into the small dimensions of a tube. As a result, polymer tubes formed by conventional extrusion methods tend to possess a significant degree of longitudinal orientation. However, conventionally extruded tubes tend to possess no or substantially no orientation in the circumferential direction.

Several embodiments of manufacturing implantable medical devices with biaxial orientation may include the use of a forming apparatus, such as an extruder. Representative examples of forming apparatuses for the present invention may include single screw extruders, intermeshing co-rotating and counter-rotating twin-screw extruders and other multiple screw masticating extruders.

Certain embodiments of manufacturing an implantable medical device with a forming apparatus may include radial expansion of an annular polymer film. In one embodiment, a method may include introducing a polymer into a forming apparatus that includes a first annular member disposed within a second annular member. The first annular member may be a mandrel and the second annular member may be a die. The polymer may be conveyed through an annular chamber as an annular film between the annular members. In some embodiments, the annular polymer film may be a polymer melt at a temperature above $T_m$ of the polymer.

In one embodiment, the introduced polymer may be at a temperature above a $T_m$ of the polymer. Alternatively, the introduced polymer may be at a temperature below a $T_m$ of the polymer. The forming apparatus may be configured to melt the polymer. In another embodiment, the polymer may be introduced in a mixture that includes the polymer and a solvent. As the mixture is conveyed through the apparatus as an annular film, at least some of the solvent may be vaporized and removed from the apparatus. Representative examples of solvents may include chloroform, acetone, chlorobenzene, ethyl acetate, 1,4-dioxane, ethylene dichloride, 2-ethyhexanol, and combinations thereof.

Some embodiments may further include radially expanding the annular film. In one embodiment, the annular film may be expanded after exiting from the apparatus. In an embodiment, the annular film may be expanded with a gas at a selected pressure. The gas may be conveyed through a second annular chamber within the first annular member. A tube may then be formed from the expanded annular film. In an embodiment, the radial expansion may induce circumferential orientation in the annular film, and hence in the resulting tube.

The method may further include fabricating an implantable medical device from the tube. The fabricated device may have at least one mechanical property more desirable than an equivalent device fabricated from an equivalent polymer tube formed from an annular film without radial expansion. The dimensions of the polymer tube are equal to dimensions of the equivalent polymer tube formed from an annular film without radial expansion. Additionally, the fabrication of the equivalent device from the equivalent polymer tube is the same as the fabrication of the device from the polymer tube.

The induced molecular orientation may result in more desirable mechanical properties such as greater circumferential strength and/or greater rigidity. In general, the radial expansion may be controlled to obtain a desired property of the implantable medical device. For example, the pressure of the gas and the temperature of the annular film influence the radial expansion.

In an embodiment, the expanded annular film may be drawn to a desired diameter subsequent to radial expansion. In some embodiments, the annular film may be drawn by a puller. The puller may include a conveyor assembly that supports and sizes the annular film. The expanded annular film may be cooled during expansion and/or after drawing. For example, the annular film may be conveyed through a water bath at a selected temperature. Alternatively, the annular film may be cooled by air or some other gas at a selected temperature.

As indicated above, it is desirable to cool the polymer melt to inhibit dissipation of the induced circumferential molecular orientation. In an embodiment, the cooling rate may be used to control the degree of induced molecular orientation in the polymer tube. The annular film may be cooled at or near an ambient temperature, e.g. 25° C. Alternatively, the annular film may be cooled at a temperature below ambient temperature.

In certain embodiments of the method, the gas used to expand the annular film may be conveyed through a second annular chamber within the first annular member. The gas may be air or some other conveniently available gas. The gas may be an inert gas such as argon, nitrogen, etc. The pressure of the gas may be selected to expand the annular film to a desired inside diameter and outside diameter. For example, the flow of the gas may be configured to expand the annular film to an outer diameter larger than the second annular member and an inner diameter larger than the first annular member. In addition, the pressure of the gas may be controlled to obtain a desired property or a desired improvement of a property of the implantable medical device. For example, the greater the radial expansion, the more circumferential molecular orientation may be induced in the annular film. Furthermore, the drawing speed may also be controlled to obtain a desired degree of induced circumferential orientation. As the drawing speed is increased, the degree of induced circumferential orientation decreases.

It is desirable for the temperature of the annular film during expansion to be greater than the melting temperature of the polymer. As discussed above, the higher the temperature, the greater the segmental mobility of polymer chains. Therefore, temperature may be used to control the degree of molecular orientation in the annular film, and hence, to obtain desired mechanical properties of the implantable medical device.

Figure 3:
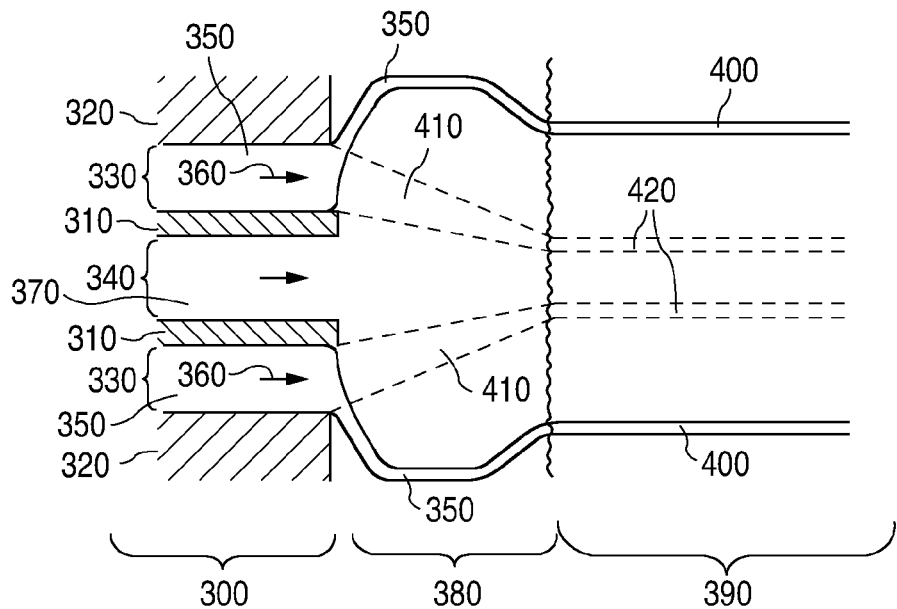
FIG. 3 depicts a system and method of manufacturing an implantable medical device.

FIG. 3 illustrates an example of a system and method of manufacturing an implantable medical device that uses radial expansion to induce circumferential molecular orientation. FIG. 3 depicts an axial cross-section of a portion of a forming apparatus 300. Forming apparatus 300 includes a first annular member 310, a second annular member 320, a first annular chamber 330, and a second annular chamber 340. Molten polymer in the form of an annular film 350 is conveyed through annular chamber 330 in the direction of arrows 360. A gas stream 370 at a selected pressure is conveyed through second annular chamber 340. Annular film 350 is exits from forming apparatus 300 to an expansion region 380. Annular film 350 is radially expanded by gas 370 as it exits forming apparatus 300. As shown, annular film 350 is expanded to a diameter greater than the outer diameter of first annular member 310 and the inner diameter of the second annular member 320. Annular film 350 is then drawn into a cooling region 390 to form a polymer tube 400. For the purpose of comparison, FIG. 3 also depicts an annular film 410 formed without radial expansion. A polymer tube 420 formed from an annular film 410 is also depicted.

Certain embodiments of manufacturing an implantable medical device with a forming apparatus may include inducing circumferential orientation by applying shear stress to a polymer. An embodiment of a method for manufacturing an implantable medical device may include introducing a polymer into a forming apparatus with a first annular member disposed within a second annular member. The first annular member may be a mandrel and the second annular member may be a die. The polymer may be conveyed through an annular chamber as an annular film between the annular members. In some embodiments, the annular polymer film may be a polymer melt at a temperature above a $T_m$ of the polymer.

In one embodiment, the introduced polymer may be at a temperature above a $T_m$ of the polymer. Alternatively, the introduced polymer may be at a temperature below a $T_m$ of the polymer. The forming apparatus may be configured to melt the polymer. In another embodiment, the polymer may be introduced in a mixture that includes the polymer and a solvent. As the mixture is conveyed through the apparatus as an annular film, at least some of the solvent may be vaporized and removed from the apparatus.

In some embodiments, the method may further include inducing circumferential flow in the annular film. A polymer tube may be formed from the annular film. It is advantageous for the temperature of the annular film to be greater than the melting temperature of the polymer. The annular film may be removed from the forming apparatus.

In an embodiment, the induced circumferential flow may induce circumferential orientation in the annular film, and hence in the resulting polymer tube. Some embodiments may then include fabricating an implantable medical device from the polymer tube.

In certain embodiments, a mechanical property of the device may be more desirable than a mechanical property of an equivalent device formed from a polymer tube formed from an annular polymer film formed without circumferential flow. The dimensions of the polymer tube are equal to dimensions of the equivalent polymer tube formed from an annular polymer film formed without circumferential flow. Additionally, fabrication of the equivalent device from the equivalent polymer tube is the same as the fabrication of the device from the polymer tube. The induced molecular orientation may result in more desirable mechanical properties such as greater circumferential strength and/or greater modulus or rigidity. In general, the circumferential flow may be controlled to obtain a desired property of the implantable medical device.

In an embodiment, the annular film subjected to circumferential flow may be drawn to a desired diameter. The annular film may also be cooled during expansion and/or after drawing in the manner described above.

Various embodiments of a method of inducing circumferential orientation may be distinguished by the manner of inducing circumferential flow. Several embodiments may include inducing circumferential flow in the annular film by rotating the first annular member, the second annular member, or both annular members. It is expected that counter-rotation of both the first annular member and the second annular member may induce the greatest shear on the annular film, and hence, induce the greatest circumferential orientation. In some embodiments, the degree of induced orientation may be controlled by parameters such as the rotation speed and relative rotation speed of the annular members.

In certain embodiments, circumferential flow may be induced by a spiral channel on at least a portion of a surface of the rotating first annular member and/or the rotating second annular member. The spiral channel may tend to induce spiral circumferential molecular orientation in the annular polymer film.

Moreover, drawing the annular film may influence the induced circumferential molecular orientation. Typically, the annular polymer film is exposed to air at ambient temperature while it is being drawn. As a result, the annular film tends to cool as it is drawn. The cooling may cause dissipation in molecular orientation in the annular film. Therefore, the length of a drawing region may be directly proportional to a cooling rate of an annular film, and hence, the dissipation of molecular orientation. The rotational speed of annular member(s) may compensate for the dissipation in molecular orientation due to cooling. However, the rotational speed of annular members(s) is limited since the annular members may become unstable at sufficiently high rotation speeds.

Figure 4A:
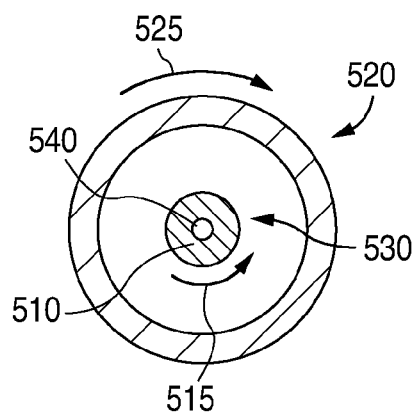
FIG. 4A depicts a radial cross-section of a forming apparatus.
Figure 4B:
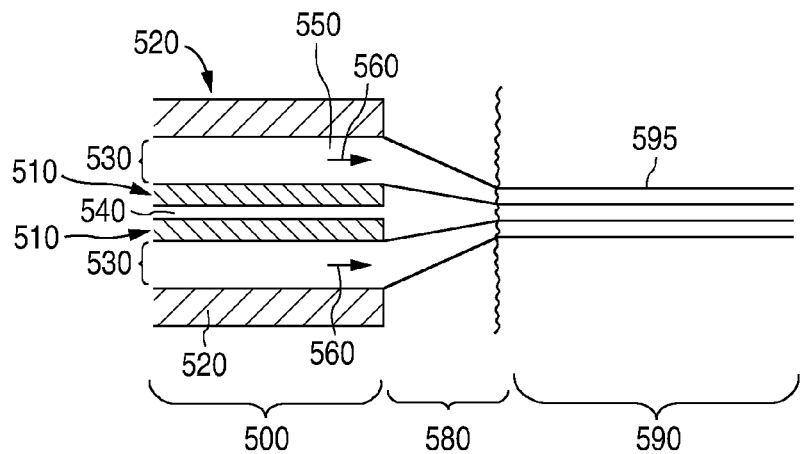

FIGS. 4A and 4B illustrate an example of a system and method of manufacturing an implantable medical device that uses circumferential flow to induce molecular orientation. FIG. 4A includes a radial cross-section of a forming apparatus 500 and FIG. 4B includes an axial cross-section of a portion of forming apparatus 500. Forming apparatus 500 includes a first annular member 510, a second annular member 520, a first annular chamber 530, and a second annular chamber 540. As depicted by FIG. 4A, first annular member 510 and second annular member 520 are configured to rotate as depicted by arrows 515 and 525, respectively. FIG. 4B shows that molten polymer in the form of an annular film 550 is conveyed through annular chamber 530 in the direction of arrows 560. Rotation of first annular member 510 and/or second annular member 520 induce circumferential flow in annular film 550. Annular film 550 is removed from forming apparatus 500 to a drawing region 580. As shown, annular film 550 is drawn to a desired diameter smaller than the diameter of second annular member 520. Annular film 550 is then drawn into a cooling region 590 to form a polymer tube 595.

In another embodiment, circumferential flow may be induced in the annular film with at least a portion of the annular film external to the apparatus. The annular film external to the apparatus may be positioned over or within a third annular member. The third annular member may be configured to rotate at least a portion of the annular film external apparatus. In an embodiment, the annular film may exit the forming apparatus and be drawn over or within the third annular member being formed into the polymer tube. The rotating portion of the annular film may induce circumferential flow, and hence, circumferential molecular orientation in the annular film from at least a point of exit from the forming apparatus to the rotating third annular member. The degree of induced orientation may be controlled by the rotation speed of the third annular member.

In certain embodiments, circumferential flow may be induced in at least a portion of the annular film external to the apparatus with at least a portion of the first annular member that is external to the apparatus. Rotation of the first annular member induces circumferential flow to at least a portion of the annular film external to the apparatus.

Figure 5:
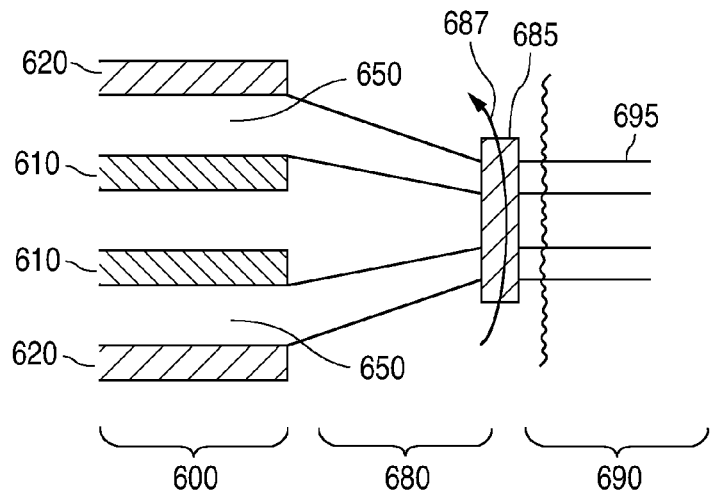

FIG. 5 illustrates another example of a system and method with induced circumferential flow similar to the system and method depicted in FIGS. 4A and 4B. FIG. 5 also depicts an axial cross-section of a portion of a forming apparatus 600, similar to forming apparatus 500 in FIGS. 4A and 4B. However, the system in FIG. 5 further includes a third annular member 685. An annular film 650 is exits from forming apparatus 600 to a drawing region 680. Annular film 650 is then positioned within third annular member 685. Third annular member 685 is configured to rotate, as shown by an arrow 687. Rotation of third annular member 685 induces circumferential flow on the portion of annular film 650 positioned on third annular member 685. Rotation of the portion of annular film 650 induces circumferential flow on the portion of annular film 650 at least in drawing region 680. As shown in FIG. 5, annular film 650 is drawn further into a cooling region 690 to form a polymer tube 695. First annular member 610 and/or second annular member 620 may also be configured to rotate. Rotation of first annular member 610 and/or second annular member 620 may induce circumferential flow in annular film 650 within forming apparatus 600.

Figure 6:
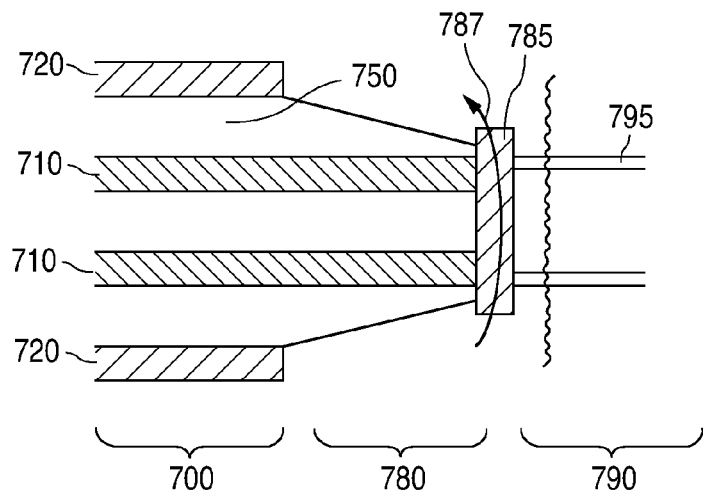

FIG. 6 illustrates another example of a system and method with induced circumferential flow similar to the system and method depicted in FIG. 5. FIG. 6 also depicts an axial cross-section of a portion of a forming apparatus 700, similar to forming apparatus 600 in FIG. 5. However, the system in FIG. 5 includes a first annular member 710 that extends axially external to forming apparatus 700. An annular film 750 is exits from forming apparatus 700 to a drawing region 780. Annular film 750 is then positioned within a third annular member 785. Third annular member 785 is configured to rotate, as shown by an arrow 787. Rotation of third annular member 785 induces circumferential flow on the portion of annular film 750 positioned on third annular member 785. Rotation of the portion of annular film 750 induces circumferential flow on the portion of annular film 750 at least in a drawing region 780. As shown in FIG. 6, annular film 750 is drawn further into a cooling region 790 to form polymer tube 795. First annular member 710 and/or second annular member 720 may also be configured to rotate. Rotation of first annular member 710 may induce circumferential flow in annular film 750 within forming apparatus 700 and within drawing region 780. Rotation of annular member 720 may induce circumferential flow in annular film 750 within forming apparatus 700.

In a further embodiment, circumferential flow in the annular film may be induced by rotating the polymer tube. The polymer tube may be rotated by positioning the polymer tube over or within a third annular member that is configured to rotate the polymer tube. The annular film may be cooled to form the polymer tube. The rotating polymer tube may induce circumferential flow, and hence, circumferential orientation in the annular film from the polymer tube to at least the point of exit of the annular film from the apparatus.

Figure 7:
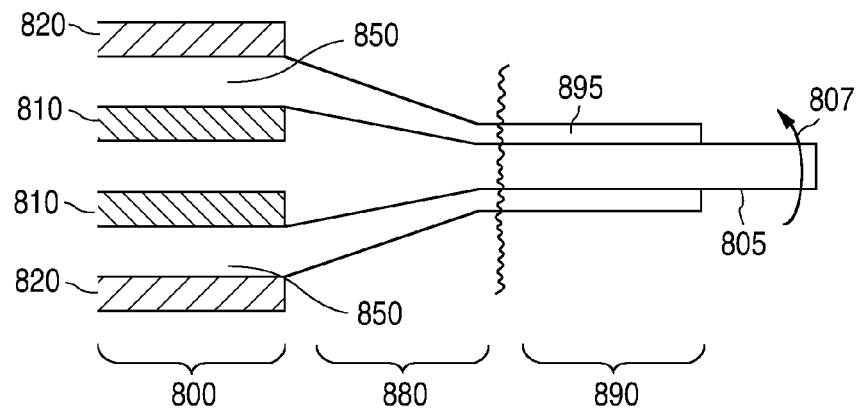

FIG. 7 illustrates another example of a system and method with induced circumferential flow similar to the system and method depicted in FIGS. 4-6. FIG. 7 also depicts an axial cross-section of a portion of a forming apparatus 800, similar, for example, to forming apparatus 500 in FIG. 4B. However, the system in FIG. 7 includes a fourth annular member 805. An annular film 850 is exits from forming apparatus 800 to a drawing region 880. As shown in FIG. 7, annular film 850 is drawn into a cooling region 890 to form a polymer tube 895. Polymer tube 895 is positioned on fourth annular member 805. Fourth annular member 805 is configured to rotate, as shown by an arrow 807. Rotation of fourth annular member 805 rotates polymer tube 895 which induces circumferential flow on the portion of annular film 850 at least in drawing region 880. First annular member 810 and/or second annular member 820 may also be configured to rotate to induce circumferential flow.

Furthermore, some embodiments that include inducing circumferential orientation in a method of manufacturing implantable medical devices may include application of stress to a polymer at temperatures less than or equal to a $T_m$ of the polymer. For example, circumferential molecular orientation in a polymer tube may be induced after fabrication of a tube.

Certain embodiments of a method of manufacturing an implantable medical device may include radially expanding a tube about a cylindrical axis of the tube from a first diameter to a second diameter. Some embodiments may include expanding a polymer tube plastically beyond the yield point or elastic limit of the polymer. The radial expansion of the polymer tube may induce circumferential molecular orientation, and hence, desired circumferential strength and modulus or rigidity in the polymer tube. As indicated above, a polymer expanded beyond its yield point tends to retain its expanded configuration, and hence, tends to retain the induced molecular orientation. An implantable medical device may then be fabricated from the expanded tube having a second diameter which is greater than the first diameter. An implantable medical device may then be fabricated from the expanded tube having a second diameter greater than the first diameter.

In certain embodiments, the tube may be expanded radially by application of radial pressure. It may be desirable apply a pressure less than about an ultimate stress of the polymer to inhibit or prevent damage to the tube. In some embodiments, radial pressure may be applied to the polymer tube by positioning the tube within an annular member and conveying a gas at a selected pressure into a proximal end of the polymer tube. A distal end of the polymer tube may be closed. The end may be open in subsequent manufacturing steps. The annular member may act to control the diameter of the expanded tube by limiting the expansion to the inside diameter of the annular member. The insider diameter of the annular member may correspond to a desired diameter of the tube. Alternatively, the pressure of the conveyed gas may be used to control the expansion of the tube to a desired diameter.

Some embodiments may include applying heat to the tube to facilitate radial expansion of the tube. In some embodiments, the tube may be heated prior to, contemporaneously with, and/or subsequent to applying radial pressure to the tube. In one embodiment, the tube may be heated by conveying a gas at a temperature greater than an ambient temperature on and/or into the tube.

Some embodiments may include cooling the expanded tube prior to fabrication of the medical device. The expanded tube may be cooled at a temperature below an ambient temperature. Alternatively, cooling the expanded polymer tube may include cooling the expanded polymer tube at a temperature at or near an ambient temperature.

In an embodiment, the device may include at least one mechanical property more desirable than an equivalent device fabricated from an equivalent polymer tube formed without radial expansion. The dimensions of the expanded polymer tube are equal to dimensions of the equivalent polymer tube formed without radial expansion. In addition, fabrication of the equivalent device from the equivalent polymer tube is the same as the fabrication of the device from the cooled polymer tube.

Certain embodiments may include expanding the polymer tube at a temperature below a $T_g$ of the polymer. Other embodiments may include expanding the polymer tube in a temperature range greater than or equal to a $T_g$ of the polymer and less than or equal to a $T_m$ of the polymer. Below $T_m$, the polymer tube may retain its cylindrical shape even with applied pressure.

In certain embodiments, the radial expansion may be controlled to obtain a desired degree of induced molecular orientation, and hence, a desired property of the implantable medical device. For example, the applied pressure, temperature of the polymer tube, and the cooling rate of the polymer tube may be controlled to obtain desired properties, such as circumferential strength and/or modulus or rigidity, of the expanded polymer tube.

Figure 8A:
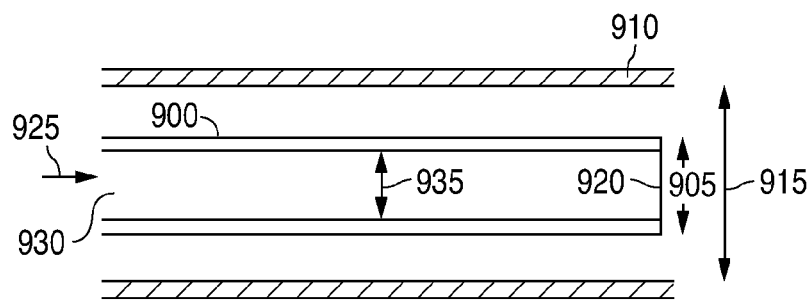
FIGS. 8A and 8B depict a method of expanding a tube.
Figure 8B:
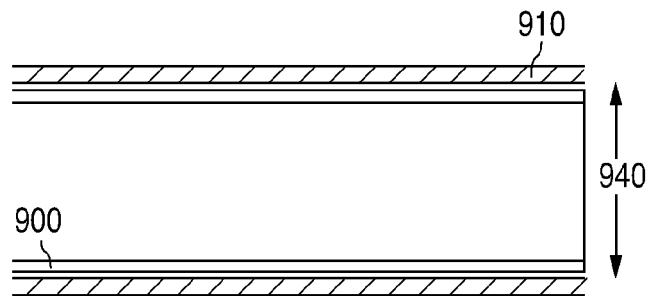

FIGS. 8A and 8B illustrate a method of expanding a polymer tube for use in manufacturing an implantable medical device. FIG. 8A depicts an axial cross-section of a polymer tube 900 with an outside diameter 905 positioned within an annular member 910. Annular member 910 may act as a mold that limits the expansion of polymer tube 900 to a diameter 915, the inside diameter of annular member 910. Polymer tube 900 may be closed at a distal end 920. Distal end 920 may be open in subsequent manufacturing steps. A gas, such as air or an inert gas, may be conveyed, as indicated by an arrow 925, into an open proximal end 930 of polymer tube 900. Polymer tube 900 may be heated by heating the gas to a temperature above ambient temperature prior to conveying the gas into polymer tube 900. Alternatively, heat may be applied to the exterior of annular member 910. The conveyed gas combined with the applied heat may act to radially expand polymer tube 900, as indicated by an arrow 935. FIG. 8B depicts polymer tube 900 in an expanded state with an outside diameter 940 within annular member 910.

As discussed above, implantable medical devices may be fabricated from tubes that are formed from planar polymer films or sheets. As used herein, a "film" or "sheet" refers to something that is thin in comparison to its length and breadth.

In certain embodiments, a tube may be formed from a film by rolling a film into a cylindrical shape. The sheet may then be bonded with a suitable adhesive. The film may be bonded at opposing edges of the film that are parallel or substantially parallel to a cylindrical axis. The film may be cut so that the formed tube is a desired diameter.

It may be desirable to form a polymer tube from a polymer film that has biaxial orientation. Polymer films or sheets may be made by several different processes. A blown film or sheet can be made by expansion and stretching of a preform or parison. The preform or parison refers to a hollow molten tube extruded from the die head of a blow molding machine expanded within the mold. In the blow molding process, air is blown into the parison and it forms a bubble. The bubble is then drawn through rollers, which stretch the film or sheet to the appropriate thickness. In another process, a polymer film may also be made by extrusion through a slit die, such as compression molding. In addition, cast film may be made from a cast-film or chill-roll extrusion process. In a cast-film process an extruded film or sheet is dimensionally stabilized by contacting it with several chrome-plated chill rolls. Blown film has some biaxial molecular orientation. Extruded film has extrusion direction molecular orientation. However, cast film typically has very little molecular orientation.

Moreover, a polymer film with a desired degree of biaxial molecular orientation may be fabricated from blown, cast, or extruded film using biaxial stretching. Certain embodiments of a method of manufacturing an implantable medical device may include stretching a film along a first axis of stretching. In some embodiments, the method may further include stretching the film along a second axis of stretching. The film may be stretched by application of a tensile force or drawing tension. The stretching of the film may induce molecular orientation in the polymer film, and hence high strength and modulus or rigidity, along the first axis of stretching and the second axis of stretching.

Certain embodiments may include fabricating an implantable medical device from the stretched film. In one embodiment, fabricating an implantable medical device from the stretched film may include forming a tube from the stretched film. Some embodiments of fabricating an implantable medical device from the stretched film may include forming a pattern having at least one strut on at least a portion of the tube. In another embodiment, a pattern may be formed on the stretched film prior to forming a tube from the stretched sheet.

A mechanical property of the device may be more desirable than a mechanical property of an equivalent device fabricated from an unstretched film. The dimensions of the device are equal to dimensions of the equivalent device formed from an unstretched polymer film. The fabrication of the equivalent device is the same as the fabrication of the device.

In certain embodiments, the stretching may be controlled to obtain a desired degree of induced molecular orientation, and hence, desired properties of the implantable medical device. The stretching may be controlled by controlling various process parameters such as tensile force used for stretching, the relative values of the tensile force applied along the axes, and the temperature of the film during stretching.

In one embodiment, a polymer film may be stretched using a tenter. In a tenter, stretching is performed inside of a box that may be temperature-controlled. Inside of the box, a film is grasped on either side by tenterhooks that exert a tensile force or drawing tension along at least one axis. The degree of stretching along the axes may be substantially equal, or alternatively, unbalanced. Therefore, the mechanical properties of a polymer tube formed from a stretched film may be controlled by the degree of stretching along each axis and also by the relative amount stretching along the axes.

Figure 9:
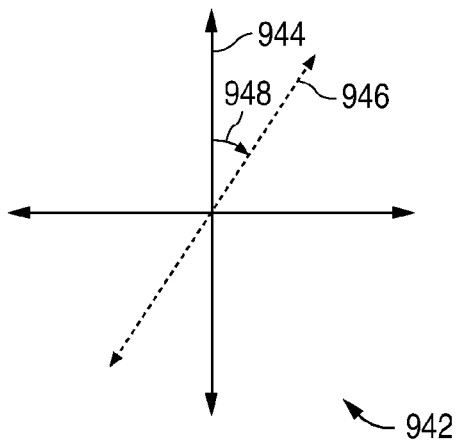
FIG. 9 depicts an x-y coordinate plane.

In certain embodiments, a tube may be formed to have a desired relative orientation of a cylindrical axis of the tube with at least one stretching axis. A cylindrical axis of a tube formed from the stretched sheet may be parallel, perpendicular, or at an angle between parallel and perpendicular to the first axis of stretching and/or the second axis of stretching. FIG. 9 depicts an x-y coordinate plane 942 for illustrating the relationship between an axis of stretching 944 and a cylindrical axis 946 of a tube formed from a stretched sheet. An angle 948 is the relative orientation between axis of stretching 944 and cylindrical axis 946.

Figure 10A:
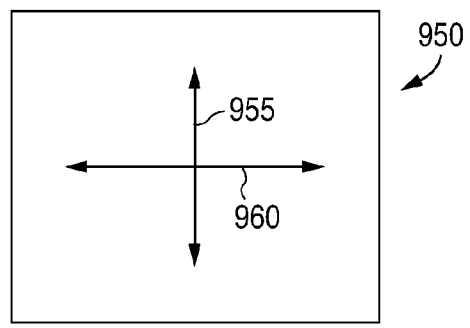
FIG. 10A depicts a film.
Figure 10B:
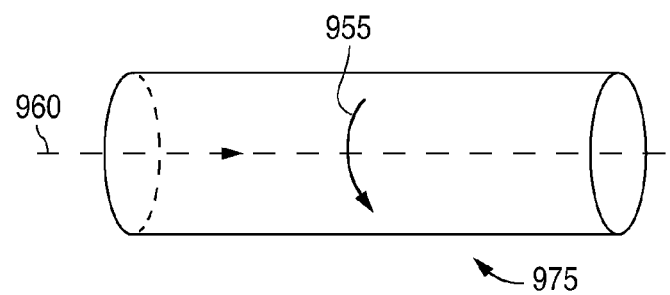
FIG. 10B depicts a tube.

It is believed that the maximum improvement in mechanical properties such as strength due to stretching or deformation for a polymer is parallel to an axis of stretching or deformation. Therefore, a tube with its cylindrical axis perpendicular to a stretching axis may provide maximum circumferential strength of a tube, and hence, a device manufacturing from the tube. FIG. 10A illustrates a polymer film 950 that has been stretched along two axes indicated by arrows 955 and 960 to have biaxial molecular orientation. FIG. 10B depicts a polymer tube 975 formed from polymer film 950. Polymer tube 975 is formed so that the axes depicted by arrows 955 and 960 in FIG. 10A are along the radial direction and cylindrical axis of polymer tube 975, respectively.

In some embodiments, the film may be stretched plastically beyond the yield point or elastic limit of the polymer along the first axis of stretching and/or the second axis of stretching. However, it may be desirable to stretch with a force that applies a stress that is less than an ultimate stress of the polymer to inhibit or prevent damage to the film.

Alternatively, the polymer tube may be stretched elastically. After stretching, an elastically stretched film may be cooled relatively quickly to inhibit contraction and dissipation of induced molecular orientation. For example, the stretched film may be cooled at a temperature substantially below an ambient temperature.

In one embodiment, a polymer film may be stretched at a temperature greater than or equal to a $T_g$ and less than or equal to a $T_m$ of the polymer. Below a $T_m$, a planar polymer film may retain its shape even with applied tensile force or tension. In another embodiment, the film may be stretched at a temperature less than or equal to a $T_g$ of the polymer. Additionally, the temperature of the film may be controlled to obtain desired properties, such as circumferential strength and/or modulus or rigidity, of a polymer tube formed from the stretched film.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a stent, comprising:
   introducing a polymer into a forming apparatus comprising a first annular member disposed within a second annular member, wherein the polymer is conveyed through an annular chamber as an annular film between the annular members,
   wherein the polymer comprises a bioabsorbable polymer;
   inducing circumferential flow in the polymer conveyed through the annular chamber as the annular film;
   forming a tube from the annular film; and
   fabricating a scaffold comprising a plurality of interconnecting struts from the tube.

2. The method of claim 1, wherein the introduced polymer is at a temperature above a melting temperature of the polymer.

3. The method of claim 1, wherein the introduced polymer is at a temperature below a melting temperature of the polymer, and wherein the forming apparatus is configured to melt the polymer.

4. The method of claim 1, wherein the polymer is introduced in a mixture comprising the polymer and a solvent.

5. The method of claim 1, wherein the annular film is at a temperature above a melting temperature of the polymer.

6. The method of claim 1, wherein the forming apparatus comprises an extruder.

7. The method of claim 1, wherein the circumferential flow is induced in the annular film by rotating the first annular member and/or rotating the second annular member.

8. The method of claim 7, wherein the circumferential flow is induced in the annular film by a spiral channel on at least a portion of a surface of the rotating first annular member.

9. The method of claim 7, wherein the circumferential flow is induced in the annular film by a spiral channel on at least a portion of a surface of the rotating second annular member.

10. The method of claim 1, wherein the circumferential flow is induced in the annular film with at least a portion of the annular film external to the apparatus positioned over or within a third annular member that is configured to rotate at least a portion of the annular film.

11. The method of claim 1, wherein the circumferential flow is induced in the annular film by rotating the tube.

12. The method of claim 11, wherein the tube is rotated by positioning the tube over or within a third annular member that is configured to rotate the tube.

13. The method of claim 1, wherein the circumferential flow is induced in the annular film external to the apparatus with at least a portion of the first annular member that is external to the apparatus.

14. The method of claim 13, wherein rotation of the first annular member induces circumferential flow to at least a portion of the annular film external to the apparatus.

15. The method of claim 1, further comprising drawing the annular film to a desired diameter prior to cooling the annular film.

16. The method of claim 1, further comprising cooling the annular film at or near an ambient temperature.

17. The method of claim 1, further comprising cooling the annular film below an ambient temperature.

18. A method of manufacturing a stent, comprising:
   introducing a polymer into a forming apparatus comprising a first annular member disposed within a second annular member, wherein the polymer is conveyed through an annular chamber as an annular film between the annular members;
   inducing spiral circumferential molecular orientation in the annular polymer film with a spiral channel on at least a portion of a surface of the first annular member or the second annular member;
   forming a tube from the annular film; and
   fabricating a scaffold comprising a plurality of interconnecting struts from the tube.

19. The method of claim 18, wherein the first annular member and/or the second annular member rotate.

* * * * *